United States Patent [19]

Murib et al.

[11] Patent Number: 4,769,507

[45] Date of Patent: Sep. 6, 1988

[54] PROCESS FOR MAKING HIGHER HYDROCARBONS FROM METHANE

[75] Inventors: Jawad H. Murib, Cincinnati; John H. Kahn, Wyoming, both of Ohio

[73] Assignee: National Distillers and Chemical Corporation, Cincinnati, Ohio

[21] Appl. No.: 31,805

[22] Filed: Mar. 30, 1987

[51] Int. Cl.$^4$ ................................................. C07C 2/10
[52] U.S. Cl. .................................... 585/500; 585/661; 585/417; 585/418; 585/656
[58] Field of Search ............... 585/500, 654, 415, 417, 585/418, 656, 658, 661

[56] References Cited

U.S. PATENT DOCUMENTS

| | | | |
|---|---|---|---|
| 3,979,332 | 9/1976 | Kiovsky | 502/229 |
| 4,239,658 | 12/1980 | Mitchell, III et al. | 585/943 |
| 4,620,057 | 10/1986 | Kimble et al. | 585/943 |
| 4,665,261 | 5/1987 | Mazurek | 585/943 |
| 4,731,494 | 3/1988 | Murib | 570/244 |

*Primary Examiner*—William R. Dixon, Jr.
*Assistant Examiner*—James M. Hunter, Jr.
*Attorney, Agent, or Firm*—Kenneth D. Tremain

[57] ABSTRACT

A process for making hydrocarbons of at least two carbon atoms from methane is disclosed. In this process methane and a source of oxygen are introduced into a molten salt, maintained at a temperature in the range of between about 660° C. and about 800° C., comprising at least one metal iodide, the metal of which is selected from the group consisting of alkali metals, alkaline earth metals and mixtures thereof and a catalyst comprising at least one metal selected from the group consisting of metals of Group IB and Group VIII of the Periodic Table of the Elements. The methane and oxygen source are introduced into the mixture such that they do not contact each other.

21 Claims, No Drawings

PROCESS FOR MAKING HIGHER HYDROCARBONS FROM METHANE

BACKGROUND OF THE DISCLOSURE

1. Field of the Invention

The present invention is directed to a process for making higher hydrocarbons from methane. More particularly, the present invention is directed to a process for making hydrocarbons having at least two carbon atoms in which methane and a source of oxygen are separately introduced into a melt including a molten metal iodide salt containing a catalyst comprising at least one metal selected from the group consisting of the metals of Group IB and Group VIII of the Periodic Table of the Elements.

2. Background of the Prior Art

Processes for synthesizing higher hydrocarbons, that is, hydrocarbons containing at least two carbon atoms, whether saturated or not, from methane have been a continuing aim of those skilled in the art. This is to be expected in that methane is readily available at low cost. Conversion of methane into higher hydrocarbons, which are themselves useful as intermediates in the synthesis of valuable end products, represents an obviously desirable pursuit. It is thus not surprising that many processing schemes have been devised for synthesizing higher hydrocarbons, for example, ethylene and ethane, from methane.

G. E. Keller et al., *Journal of Catalysis*, Vol. 73, 9–19 (1982) provides a method of synthesizing ethylene by means of the oxidative coupling of methane. In this teaching methane is converted, in a gas phase reaction, to ethylene and ethane at atmospheric pressure and at temperatures ranging from 500° C. to 1000° C. in the presence of a catalyst which is selected from the group consisting of an oxide of tin, lead, bismuth, antimony, tellurium, cadmium and manganese. In all cases, the catalyst is supported on alumina. It is also noted that this study indicates that Group VIII metals demonstrate very little or no catalytic activity in this reaction.

U.S. Pat. No. 4,465,893 issued to Olah discloses a process for the direct conversion of methane or natural gas, which is predominantly methane, to gasoline range hydrocarbons. In this heterogeneous gas-phase reaction, the methane or natural gas feed is condensed in the presence of a higher valence Lewis acid halide, preferably tantalum pentafluoride, niobium pentafluoride or antimony pentafluoride, supported by a carrier which is preferably fluorinated. This condensation reaction preferably occurs in the presence of an oxidizing agent such as oxygen.

A whole plurality of patents issued to Jones et al. disclose a method for converting methane to higher hydrocarbon products which comprises contacting methane and a reducible oxide of antimony, germanium, bismuth, lead, indium, manganese or tin in U.S. Pat. Nos. 4,443,644; 4,443,645; 4,443,646; 4,443,647; 4,443,648; 4,443,649; and 4,444,984, respectively. In addition, U.S. Pat. No. 4,495,374, also issued to Jones et al., recites the same process generically wherein methane contacts at least one reducible oxide of at least one metal and is converted to higher hydrocarbon products.

U.S. Pat. No. 4,450,310 to Fox et al. describes a process for converting methane to olefins and hydrogen at 500° C. wherein methane, in the absence of oxygen and water, is contacted with a catalyst comprising the mixed oxide of a first metal selected from lithium, sodium, potassium, rubidium, cesium and mixtures thereof, a second metal selected from beryllium, magnesium, calcium, strontium, barium and mixtures thereof and, optionally, a promoter metal selected from the group consisting of copper, rhenium, tungsten, zirconium, rhodium and mixtures thereof. This gas phase reaction preferably occurs at a temperature of between about 700° C. to about 1000° C.

U.S. Pat. No. 4,199,533 to Benson describes a gas phase reaction for converting methane into higher molecular weight hydrocarbons by using chlorine gas as a recycleable reactant. Thus, this reaction occurs at a temperature in the range of between 700° and 1710° C. without a catalyst.

U.S. Pat. No. 4,172,810 to Mitchell, III et al. sets forth regenerable catalyst-reagents and a process for using these catalyst-reagents for the conversion and oligomerization of hydrocarbons, particularly methane, at relatively low temperatures to produce products rich in ethylene, benzene or both, in admixture with other hydrocarbons. The catalyst-reagents of this invention, which can be used in this gas phase conversion of methane, include a Group VIII noble metal having an atomic number of 45 or greater, nickel or a Group IB noble metal having an atomic number of 47 or greater; a Group VIB metal oxide; and a Group IIA alkaline earth metal, composited with a suitably passivated, spinel-coded refractory support, preferably alumina. In a preferred embodiment, alumina is coated with $MgAl_2O_4$ and impregnated with magnesium, chromium and platinum and thereafter calcined. Such a catalyst converts methane at 1300° F. to a mixture containing ethylene and benzene.

In addition to the above described gas phase catalytic reactions of methane to produce higher hydrocarbons, a whole body of work has been directed to the formation of olefins and diolefins by the dehydrogenation of hydrocarbons to unsaturated hydrocarbons. In this work a gaseous hydrocarbon, preferably ethane, and oxygen are introduced into a molten salt comprising at least one metallic iodide. Such a disclosure is made in U.S. Pat. No. 3,080,435 to Nager. A survey article of this technology is also provided in Adams et al., *Journal of Organic Chemistry*, Vol. 42, 1–6 (1977).

Although this technology is directed to starting hydrocarbons having at least two carbon atoms, and thus excludes methane, an allegation is made in the Nager patent that methane may be converted to ethylene and acetylene by coupling. As will be seen below, the teaching of this patent does not produce ethylene from methane.

The above review of the art emphasizes the many proposed routes for forming higher hydrocarbons from methane. That so many proposals have been made for this synthesis suggests that none of these methods have met with complete commercial success. Thus, the need for a simple process to convert methane to higher hydrocarbons still remains to be discovered.

SUMMARY OF THE INVENTION

A new process for converting methane to higher hydrocarbons containing at least two carbon atoms has now been discovered. This process represents an advance in the art in that it provides this conversion in high selectivity. That is, a new liquid-phase reaction, conducted at ambient pressure or above, has been developed which is an advance over the proposed processes of the prior art.

In accordance with the present invention a process for the manufacture of at least one hydrocarbon having at least two carbon atoms is described. In this process methane and a source of oxygen are separately introduced into a molten salt maintained at a temperature in the range of between about 660° C. and about 800° C., comprising an iodide of a metal selected from the group consisting of alkali metals, alkaline earth metals and mixtures thereof and a catalyst comprising at least one metal selected from the group consisting of metals of Group IB and Group VIII of the Periodic Table of the Elements. The process is limited by the requirement that the methane and source of oxygen do not contact each other.

DETAILED DESCRIPTION

In the process of the present invention methane is converted to at least one hydrocarbon having at least two carbon atoms. Of the higher hydrocarbons in the product stream of the process of this invention the inclusion of ethylene is particularly preferred. In addition, ethane is usually present in the product of the reaction. Further, hydrocarbons of three or more carbon atoms may also be synthesized in this process.

In this process methane and a source of oxygen are separately introduced into a molten salt which comprises an iodide of a metal selected from the group consisting of alkali metals, alkaline earth metals and mixtures thereof and a catalyst comprising at least one metal selected from the group consisting of metals of Group IB and Group VIII of the Periodic Table of the Elements. As discussed below this process is limited by the requirement that the methane and the source of oxygen not contact each other.

Those skilled in the art are aware of the danger of methane combustion and flammability. Specifically, contact between the reactants, methane and a source of oxygen, usually air or oxygen, must be avoided. Not only is there a concentration range in which these two gases explode but even if contact occurs outside the explosive range, the reaction of methane and oxygen results in the formation of carbon oxides, correspondingly reducing the formation of the desired products, hydrocarbons having at least two carbon atoms.

To prevent the undesirable reaction of methane and a source of oxygen, the reaction is preferably carried out in a "loop" reactor wherein the reaction medium is continuously circulating between two reaction zones as described in applicant's copending application, U.S. patent application, Ser. No. 031,828, filed Mar. 30, 1987, the disclosure of which is incorporated herein by reference. In a loop reactor methane is introduced into a first reaction zone and a source of oxygen is introduced into a second reaction zone thereby preventing direct contact between the two gases.

The process of the present invention occurs at temperature in the range of about 650° C. and about 1000° C. That is, the temperature of the melt is in this range. Since the process of the present invention occurs at atmospheric or higher pressure, it is obvious that the metal iodide is molten during the process. More preferably, the temperature of the molten salt, and hence the temperature of the process of this invention, is in the range of between about 660° C. and about 800° C. Most preferably, the temperature of the process of the present invention is in the range of between about 675° C. and about 750° C.

Turning to the molten salt, it comprises at least one molten metal iodide, the metal of which is selected from the group consisting of alkali metals, alkaline earth metals and mixtures thereof. More preferably, the molten salt comprises at least one molten metal iodide, the metal of which is selected from sodium, potassium, lithium, calcium, magnesium and mixtures thereof. Still more preferably, the reaction medium comprises at least one molten metal iodide wherein the metal or metals are selected from the group consisting of sodium, potassium and lithium. Most preferably, the metal iodide is lithium iodide.

The molten salt, in a preferred embodiment, also includes a metal hydroxide. The metal of the metal hydroxide is again selected from the group consisting of alkali metals, alkaline earth metals and mixtures thereof. As in the case of the iodide, the metal of the hydroxide is preferably sodium, potassium, lithium, calcium, magnesium or mixtures thereof. More preferably, the metal of the metal hydroxide is sodium, potassium or lithium. In this preferred embodiment wherein a hydroxide is provided, the most preferred hydroxide is lithium hydroxide.

It is emphasized that although the metal of the hydroxide can be the same or different as that of the iodide, it is preferable that the metal or metals of the hydroxide be identical with the metal or metals of the molten metal iodide.

In the preferred embodiment wherein the molten salt includes a mixture of metal iodide and a metal hydroxide, the molar ratio of metal iodide to metal hydroxide is in the range of between about 5:1 and about 80:1. More preferably, the molar ratio of metal iodide to metal hydroxide is in the range of between about 10:1 and about 20:1.

The catalyst utilized in the process of the present invention to produce at least one hydrocarbon having at least two carbon atoms, as stated above, comprises a metal selected from the group consisting of the metals of Group IB and Group VIII of the Periodic Table of the Elements. Of the Group IB metals, gold, silver and copper, copper and silver are preferred. Of the Group VIII metals, utilizable as catalyst of the present invention, ruthenium, platinum, palladium, rhodium and mixtures thereof are preferred.

Independent of the identity of the metal, it is preferred that the catalytic metal be added in the elemental form, that is, as the metal itself, as an oxide or as an iodide. Mixtures of two or more of the above-preferred metals or metal compounds are equally preferred. Thus, the catalyst of the present invention is preferably selected from the group consisting of copper, copper iodide, copper oxide, silver, silver iodide, silver oxide, ruthenium, ruthenium iodide, ruthenium oxide, platinum, platinum iodide, platinum oxide, palladium, palladium iodide, palladium oxide, rhodium, rhodium iodide, rhodium oxide and mixtures thereof.

Of the above preferred metals, copper- or ruthenium-containing metals are particularly preferred. Thus, a catalyst selected from the group consisting of copper, ruthenium, ruthenium oxide, ruthenium iodide and mixtures thereof is highly desireable.

In a preferred embodiment of the process of this invention, the catalytic agent is provided on an inert support. In the case where a support is provided, the inert material of the support is preferably alumina, titania, zirconia and mixtures thereof. Of these inert materials, alumina is particularly preferred.

Of all the catalysts, supported or unsupported, within the contemplation of this invention the most preferred catalysts are ruthenium iodide, ruthenium supported on alumina, ruthenium oxide and mixtures thereof.

In a preferred embodiment of the process of this invention an inert gas is additionally introduced, along with the source of oxygen, into the molten salt and catalyst. The inert gas is preferably nitrogen, carbon dioxide, a gas of Group VIII A of the Periodic Table of the Elements, such as helium, neon or argon, or mixtures thereof. Of the inert gases within the process of this invention, nitrogen is particularly preferred.

It is preferred that steam be excluded from the feed in this reaction. For reasons not totally understood, the presence of steam prevents the formation of significant amounts of ethylene, ethane and other hydrocarbons. The addition of steam results in the formation of methyl iodide. This phenomenum is more completely described in copending application, U.S. Ser. No. 031,804, filed Mar. 30, 1987.

The following examples are provided to illustrate the present invention. In that these examples are provided for illustrative purposes only, the scope of this invention should not be limited thereto.

EXAMPLE 1

A loop reactor, having two vertical conduits (1.6 cm ID by 30 cm length) and connected by upper and lower conduits, was charged with a powdered mixture of 346 g. lithium iodide, 7.7 g. lithium hydroxide, and 0.96 g. of ruthenium iodide added in increments and melted down at 700° C.

Upon melting, the liquid level in the reactor was above the upper horizontal conduit. Methane gas was introduced through one of the two vertical legs of the loop reactor directly into the melt at a rate of 54 cc/min. A gaseous mixture of oxygen and nitrogen was fed into the molten reaction medium through the second vertical leg of the reactor at a feed rate of 42 cc/min of oxygen and 63 cc/min of nitrogen. Upon reaching steady state, analysis of the methane effluent, by gas chromatographic and mass spectrometric means, showed that 1.2% of the methane feed was converted with selectivities of 50% to ethylene, 41% to ethane and 9% to carbon dioxide. Analysis of the molten metal salt indicated absence of elemental carbon or carbonates.

It is noted that in this and in the following examples percent conversion of methane is defined by the moles of methane consumed, that is, the number of moles of each product formed multiplied by the number of carbon atoms in the product, divided by the moles of methane introduced into the reaction and multiplying this ratio by 100.

The percent selectivity of a product is defined by the moles of the product multiplied by the number of carbon atoms in the product divided by the moles of methane consumed in the reaction and multiplied by 100. The moles of methane consumed in the reaction is the sum of each product formed multiplied by the number of carbon atoms in that product.

EXAMPLE 2

Example 1 was repeated except that the amount of ruthenium iodide was increased from 0.96 g. to 2.96 g. and the amount of lithium iodide was increased from 346 g. to 356 g.

Analysis of the methane effluent showed that 1.7% of the methane feed was converted per pass with a selectivity of 42% to ethylene, 55% to ethane and 3% to carbon dioxide.

EXAMPLE 3

Example 1 was repeated except that the amount of ruthenium iodide was increased to 5.4 g. and the amount of lithium iodide was increased to 366 g.

Analysis showed that 3.2% of the methane feed was converted per pass with selectivities of 66% to ethylene, 31% to ethane and 3% to carbon dioxide.

EXAMPLE 4

Example 3 was repeated with the exception that the methane leg of the reactor was equipped with a multi-blade propeller to provide better gas-liquid contact and to pump the liquid reaction medium downward in a direction counter-current to the upward methane flow. In addition, the methane feed rate was reduced to 24 cc/min. Gaseous oxygen and nitrogen were similarly introduced through the other vertical leg, each at the rate of 12 cc. per minute.

Analysis of the methane effluent showed that 5.3% of the methane feed was converted per pass with selectivities of 81% to ethylene, 9% to ethane, 3% to propylene, 3% to butadiene and 4% to carbon dioxide. Thus, the overall selectivity to higher hydrocarbons was 96 percent.

EXAMPLE 5

Example 1 was repeated except that the catalyst of Example 1, ruthenium iodide, was replaced with three grams of 5 percent ruthenium on alumina. In this example the feed rate of methane was decreased from 54 cc/min to 40 cc/min. The feed rate of oxygen and nitrogen, into the other leg of the reactor, was changed to 14 cc/min. and 75 cc/min, respectively.

Analysis of the methane effluent showed that 1.8% of the methane was converted per pass with selectivities of 46% to ethylene, 40% to ethane and 14% to carbon dioxide.

EXAMPLE 6

A loop reactor was charged with 384 g. LiI, 8 g. LiOH, 40 g. KI and 4 g. metallic copper and melted down at 700° C. After meltdown, methane was introduced through one of the vertical legs into the molten reaction medium at a rate of 40 cc/min. A gaseous mixture of 10 cc/min oxygen and 10 cc/min nitrogen was fed into the molten reaction medium through the other leg of the reactor.

Analysis of the methane effluent showed that 5% of the methane was converted per pass with selectivities of 82% to ethylene and 6% to ethane with the balance being benzene, $C_3$ and $C_4$ olefins and traces of methyl iodide and carbon dioxide.

EXAMPLE 7

A loop reactor equipped with a stirrer was charged with 366 g. LiI, 7.7 g. LiOH and 5.4 g. $RuI_3$ and melted down at 675 C. Methane was introduced through one of the vertical legs of the reactor into the molten reaction medium at a rate of 42 cc/min. A gaseous mixture of 10.5 cc/min. oxygen and 24 cc/min. nitrogen was fed into the molten reaction medium through the other leg of the reactor.

Analysis of the methane effluent showed 2.4% of the methane was converted per pass with selectivities of 52% to ethylene, 33% to ethane and 15% to carbon dioxide.

COMPARATIVE EXAMPLE 1

Example 2 was duplicated except that the ruthenium iodide catalyst was omitted. Analysis of the gaseous product stream yielded a methane conversion rate of 0.3 percent per pass with selectivities to 21 percent ethylene and 79 percent carbon dioxide.

The results of this comparative example establish that the presence of a catalyst within the contemplation of this invention is critical to achieving good conversion and high selectivity.

COMPARATIVE EXAMPLE 2

Example 1 was repeated except that the ruthenium catalyst was omitted and the feed rates were 40 cc/min. methane through one leg of the reactor and 10 cc/min. of oxygen through the second leg. In addition, 25 cc/min. of steam was fed through the second leg, along with the oxygen.

Analysis of the methane effluent showed that 0.7% of the methane was converted to carbon dioxide without formation of $C_2$ or higher hydrocarbons.

This example establishes the detrimental effect of steam on the process of this invention to make higher hydrocarbons from methane.

COMPARATIVE EXAMPLE 3

A single bubbler reactor (½ inch OD×4 inches length) was charged with a mixture of 48 g. LiI, 1 g. LiOH and 0.1 g. $RuO_2$ and the contents melted down at 700° C. A gaseous mixture of 75 mole % methane, 12.5 mole % $O_2$ and 12.5 mole % $N_2$ was bubbled into the molten reaction medium at a rate of 16 cc/min.

Analysis of the reactor effluent showed that 7% of the methane was converted with selectivities of 12% to ethylene, 5% to ethane and 83% to carbon oxides.

This result shows that methane combustion dominates when a mixed feed of reactants is used. That is, the failure to keep oxygen and methane from contacting each other eliminates the possibility of a commercially feasible process for forming higher hydrocarbons from methane.

COMPARATIVE EXAMPLE 4

Comparative Example 3 was repeated except that a mixture of potassium iodide and sodium iodide replaced lithium iodide and potassium hydroxide was substituted for the lithium hydroxide of that example. That is, the mixture of Comparative Example 3 was replaced with the following mixture: 20 g. KI, 17.9 g. NaI, 1.3 g. KOH, and 0.36 g. $RuI_3$.

Analysis of the reactor effluent demonstrated a 9.9% conversion of the methane charged at a selectivity of 9% to ethylene, 4% to ethane, and 87% to carbon oxides.

Although this is a comparative example, based on the failure to separate methane and oxygen, with the resultant failure to obtain a high selectivity to higher hydrocarbons, still the similarity of results of this example with that of Comparative Example 3 demonstrates the equivalence of alkali metal iodides and hydroxides in the process of the present invention.

COMPARATIVE EXAMPLE 5

Comparative Example 4 was repeated except that potassium hydroxide, present in the mixture of Comparative Example 4 in an amount of 1.3 g., was omitted.

Analysis of the reactor effluent indicated an 8.3% conversion of the methane. Selectivity was 6% to ethylene, 1% to ethane, and 93% to carbon oxides. The high combustion resulted from the mixed feed of methane and oxygen.

This example indicates that the addition of the hydroxide, although present in a preferred embodiment, is not essential.

The above preferred embodiments and examples illustrate the scope and spirit of the present invention. These embodiments and examples will make apparent, to those skilled in the art, other embodiments and examples. These other embodiments and examples are within the contemplation of the present invention. Therefore, the instant invention should be limited only by the appended claims.

What is claimed is:

1. A process for making hydrocarbons having at least two carbon atoms from methane comprising introducing methane and a source of oxygen into a molten salt, maintained at a temperature of at least about 660° C., comprising an iodide of a metal selected from the group consisting of alkali, metals, alkaline earth metals and mixtures thereof and a metal-containing catalyst comprising at least one metal selected from the group consisting of metals of Group IB and Group VIII of the Periodic Table of the Elements with the proviso that said methane and said source of oxygen not contact each other.

2. A process in accordance with claim 1 wherein said source of oxygen is selected from the group consisting of oxygen and air.

3. A process in accordance with claim 1 wherein said metal of said metal iodide of said molten salt is selected from the group consisting of sodium, potassium, lithium, calcium, magnesium and mixtures thereof.

4. A process in accordance with claim 1 wherein said metal-containing catalyst includes one metal selected from the group consisting of copper, silver, platinum, palladium and ruthenium.

5. A process in accordance with claim 4 wherein said metal-containing catalyst includes one metal selected from the group consisting of copper and ruthenium.

6. A process in accordance with claim 5 wherein said metal-containing catalyst is selected from the group consisting of copper, ruthenium, ruthenium oxide, ruthenium iodide and mixtures thereof.

7. A process in accordance with claim 1 wherein said metal-containing catalyst is supported on an inert material selected from the group consisting of alumina, titania, zirconia and mixtures thereof.

8. A process in accordance with claim 1 wherein a metal hydroxide where said metal is selected said molten salt, comprises a hydroxide metal is selected from the group consisting of alkali metals, alkalihe earth metals and mixtures thereof is included in said molten salt.

9. A process in accordance with claim 8 wherein the molar ratio of said metal iodide to said metal hydroxide is in the range of between about 5:1 and about 80:1.

10. A process in accordance with claim 9 wherein said molar ratio of metal iodide to metal hydroxide is in the range of between about 10:1 and about 20:1.

11. A process in accordance with claim 8 wherein said metal of said metal iodide and said metal hydroxide are the same.

12. A process in accordance with claim 1 wherein said molten salt is maintained at a temperature in the range of between about 660° C. and about 800° C.

13. A process in accordance with claim 12 wherein said molten salt is maintained at a temperature in the range of between about 675° C. and about 750° C.

14. A process in accordance with claim 1 comprising introducing an inert gas selected from the group consisting of nitrogen, carbon dioxide, gases of Group VIIIA of the Periodic Table and mixtures thereof into said molten salt.

15. A process in accordance with claim 14 wherein said inert gas is nitrogen.

16. A process for making hydrocarbons having at least two carbon atoms from methane comprising introducing methane, a source of oxygen and an inert gas into a molten salt comprising lithium iodide and a catalyst containing a metal selected from the group consisting of copper and ruthenium, said molten salt maintained at a temperature in the range of between about 660° C. and about 750° C. with the proviso that said methane and said source of oxygen not contact each other.

17. A process in accordance with claim 16 wherein said inert gas is nitrogen.

18. A process in accordance with claim 16 wherein said catalyst is selected from the group consisting of ruthenium, ruthenium iodide, ruthenium oxide and mixtures thereof.

19. A process in accordance with claim 16 wherein said catalyst is metallic copper.

20. A process in accordance with claim 16 wherein said molten salt is maintained at a temperature in the range of between about 675° C. and about. 700° C.

21. A process in accordance with claim 16 wherein said molten salt comprises lithiim hydroxide

* * * * *

UNITED STATES PATENT AND TRADEMARK OFFICE
CERTIFICATE OF CORRECTION

PATENT NO. :     4,769,507
DATED      :     September 6, 1988
INVENTOR(S):     Jawad H. Murib and John H. Kahn It is certified that error appears in the above-identified patent and that said Letters Patent is hereby corrected as shown below:

Claim 1,   line 6, delete "," following the word "alkali".

Claim 8,   lines 2 and 3, delete "said molten salt, comprises a hydroxide metal is selected".

Claim 8,   line 4, "alkalihe" should read ---alkaline---.

Claim 21,  line 2, "lithiim" should read ---lithium---.

Signed and Sealed this

Twenty-sixth Day of June, 1990

Attest:

HARRY F. MANBECK, JR.

*Attesting Officer*     *Commissioner of Patents and Trademarks*